(12) United States Patent
Lundgren et al.

(10) Patent No.: US 6,331,232 B1
(45) Date of Patent: Dec. 18, 2001

(54) DEVICE AND METHOD FOR REDUCTION OF OXIDES OF NITROGEN

(75) Inventors: Staffan Lundgren, Hindås; Edward Jobson, Romelanda; Anders Unosson, Stockholm; Per Salomonsson, Göteborg, all of (SE)

(73) Assignee: Volvo Car Corporation (SE)

( * ) Notice: Subject to any disclaimer, the term of this patent is extended or adjusted under 35 U.S.C. 154(b) by 0 days.

(21) Appl. No.: 09/242,305

(22) PCT Filed: Aug. 11, 1997

(86) PCT No.: PCT/SE97/01338

§ 371 Date: Mar. 8, 2000

§ 102(e) Date: Mar. 8, 2000

(87) PCT Pub. No.: WO98/07968

PCT Pub. Date: Feb. 26, 1998

(30) Foreign Application Priority Data

Aug. 14, 1996 (SE) .................................................... 9602975

(51) Int. Cl.[7] ................ C25B 9/00; C25C 7/00; C25D 17/00
(52) U.S. Cl. ..................... 204/265; 204/266; 422/186.04
(58) Field of Search .................................. 205/615, 617, 205/335, 337; 204/265, 266, 283; 422/186.04

(56) References Cited

U.S. PATENT DOCUMENTS 3,870,616 * 3/1975 Dempsey et al. ............... 204/228.5
4,671,863 * 6/1987 Tejeda ................................. 204/266
5,306,411 * 4/1994 Mazanec et al. ................... 204/265
5,401,372 * 3/1995 Liu et al. ............................. 204/265

FOREIGN PATENT DOCUMENTS 0 449 423 A1   10/1991   (EP) .
95/13533        5/1995    (WO) .

OTHER PUBLICATIONS

Patent Abstracts of Japan, abstract of JP,A,5–137962 (Toyota Motor Corp.), Jun. 1, 1993, abstract.

J. Nakatani, "Removal of NO in the presence of $O_2$, using electrochemical cells," Second EU–Japan Workshop, Fundamental aspects of catalysis for clean combustion, Kyoto, Japan, Oct. 30–31, 1995.

* cited by examiner

Primary Examiner—Kathryn Gorgos
Assistant Examiner—Wesley A. Nicolas
(74) Attorney, Agent, or Firm—Kilpatrick Stockton LLP

(57) ABSTRACT

Apparatus for the reduction of nitrogen oxides in gas streams are disclosed comprising an oxygen ion-conducting substrate, an anode disposed on the substrate, a cathode disposed on the substrate, and a voltage source connected to the anode and the cathode in which the cathode is comprised of gold so that the nitrogen oxides are adsorbed and dissociated on the cathode, nitrogen may recombine into nitrogen gas on the cathode, and oxygen ions are transported through the substrate from the cathode to the anode. Methods for the reduction of nitrogen oxides in gas streams are also disclosed.

19 Claims, 4 Drawing Sheets

DEVICE AND METHOD FOR REDUCTION OF OXIDES OF NITROGEN

FIELD OF THE INVENTION

The present invention relates to a device for the reduction of nitrogen oxides. More particularly, the present invention relates to a method for the reduction of nitrogen oxides. The present invention is particularly intended for use in the field of purification of exhaust gases in combustion processes, for example, in the purification of vehicle exhaust gases.

BACKGROUND OF THE INVENTION

In the field of vehicles operated by combustion engines, there is a continuing demand for low emissions of harmful substances in the exhaust gases from the vehicle's engine. These harmful substances are primarily in the form of pollutants, such as $NO_x$ compounds (NO, $NO_2$, and $N_2O$), hydrocarbons (HC) and carbon monoxide (CO). In today's vehicles having gasoline engines, purification of the exhaust gases is normally carried out by means of an exhaust catalyst, which forms part of the exhaust system, and through which the exhaust gases are guided. In a so-called three-way catalyst, a major portion of the above-mentioned harmful compounds are eliminated through known catalytic reactions.

A condition for such a catalyst to operate with an optimal degree of purification is that the engine be controlled so that stoichiometry is obtained, i.e. so that a correctly adjusted air/fuel mixture is fed to the engine during its operation. In a motor vehicle, this can be accomplished by equipping the vehicle with a lambda sensor, by means of which a value of the oxygen content in the exhaust gases can be determined and fed to a control unit, which in turn generates the correct air/fuel mixture. However, if the condition regarding stoichiometry is not fulfilled, only a limited degree of purification of the catalyst can be obtained, particularly as regards the nitrogen oxides contained in the exhaust gases.

In certain types of combustion processes, for example in connection with diesel engines and in so-called "lean burn" processes, combustion is carried out with a relatively high surplus of oxygen, the purpose of which is to reduce the fuel consumption. This means that the stoichiometry condition is not fulfilled, and no purification of harmful emissions can be obtained in an effective manner with a conventional three-way catalyst. It is true that emissions of HC and CO compounds can be reduced by means of an oxidation catalyst, but the $NO_x$ emissions still constitute a problem. For this reason, there is a demand for devices and methods for the purification of $NO_x$ compounds, and particularly in combustion processes in which an oxygen surplus is present.

As regards the harmful $NO_x$ compounds, from the article "Removal of NO in the presence of $O_2$ using electrochemical cells," J. Nakatani, Second EU-Japan Workshop, Fundamental aspects of catalysis for clean combustion, Kyoto, Japan, Oct. 30–31 1995, a device is known by means of which $NO_x$ compounds can be converted to nitrogen gas. The device therein comprises a tube of an electrolytic material with a cathode which is arranged on the outside of the tube and an anode which is arranged on the inside of the tube. Helium is guided through the tube and past the anode, whereas a sample gas comprising nitrogen oxide, gaseous oxygen and helium is guided past the cathode. By applying an electric potential, nitrogen oxide can be converted into gaseous nitrogen and oxygen on the cathode, by means of which the ionized oxygen is pumped through the electrolyte to the anode.

The known device involves a disadvantage due to the fact that it cannot operate with the intended effect at high concentrations of oxygen in the gas in which the nitrogen oxides are to be reduced. This is due to the fact that it is not capable of distinguishing the $NO_x$ compounds from oxygen to any high degree. In the known device, oxygen must be pumped away before the conversion of $NO_x$ compounds begins. This known device thus provides a reduction of $NO_x$ compounds which is entirely insignificant when the oxygen concentration reaches approximately 2%. Consequently, since the device cannot operate at high oxygen concentrations, it cannot be used in an effective manner in connection with lean combustion processes, i.e. processes involving an oxygen surplus. An example of such a process is the combustion realized in diesel engines, the exhaust gases of which have an oxygen concentration which is approximately 5 to 18%.

SUMMARY OF THE INVENTION

In accordance with the present invention, these and other objects have now been realized by the discovery of apparatus for the reduction of nitrogen oxides in a gas stream comprising an oxygen ion-conducting substrate, at least one anode disposed on the substrate, at least one cathode disposed on the substrate, and a voltage source connected to the anode and the cathode, the cathode comprising gold, whereby nitrogen oxides are adsorbed and dissociated on the cathode, nitrogen may recombine into nitrogen gas on the cathode, and oxygen ions are transported through the substrate from the cathode to the anode. Preferably, the cathode consists essentially of gold.

In accordance with one embodiment of the apparatus of the present invention, the anode comprises gold, palladium or rhodium. Preferably, the anode consists essentially of this material.

In accordance with another embodiment of the apparatus of the present invention, the cathode includes a stabilizing material. Preferably, the anode includes a stabilizing material, and most preferably, the stabilizing material comprises platinum.

In accordance with another embodiment of the apparatus of the present invention, the oxygen ion conducting substrate comprises stabilized zirconium dioxide.

In accordance with another embodiment of the apparatus of the present invention, the apparatus includes current measuring means for measuring the transport of the oxygen ions through the substrate and control means for controlling the voltage source based on the measured value of the current measuring means.

In accordance with another embodiment of the apparatus of the present invention, the apparatus includes heating means for heating the substrate. In a preferred embodiment, the voltage source comprises a first voltage source, the heating means comprises a resistance conductor, and the apparatus includes a second voltage source for the resistance conductor.

In accordance with another embodiment of the apparatus of the present invention, the anode and cathode comprise a porous material.

In accordance with another embodiment of the apparatus of the present invention, the anode and the cathode comprise a conducting pattern including a substantially linear portion and a plurality of transverse portions extending substantially perpendicularly from the substantially linear portion.

In accordance with another embodiment of the apparatus of the present invention, the substrate comprises a plurality of walls providing a plurality of adjacent ducts for guiding the gas stream, the anode and the cathode comprising coatings on at least one of the plurality of walls forming the plurality of adjacent ducts. In a preferred embodiment, the plurality of adjacent ducts comprises a first duct and a second duct adjacent to the first duct, and the walls comprise at least one inner wall of the first and second ducts, the cathode comprising a coating on the at least one inner wall of the first duct and the anode comprises a coating on the at least one inner wall of the second duct.

In accordance with another embodiment of the apparatus of the present invention, the substrate comprises a plurality of plates including a first side and a second side defining a plurality of longitudinally extending ducts for guiding the gas stream, at least one of the first and second sides of the plurality of plates comprising the cathode and the other of the first and second sides of the plurality of plates comprising the anode. In a preferred embodiment, the anode and the cathode comprise conductive patterns, and preferably the plurality of plates include at least one pair of adjacent plates, and the apparatus includes at least one of the first and second sides of the at least one pair of the adjacent plates comprises a pair of cathodes facing each other.

In accordance with another embodiment of the apparatus of the present invention, the plurality of longitudinally extending ducts including the other of the first and second sides of the at least one pair of the adjacent plates comprising the anodes are shaped so as to block the passage of the gas stream therethrough.

In accordance with another embodiment of the apparatus of the present invention, the substrate comprises a first duct comprising the anode and a second duct comprising the cathode, the first and second ducts disposed in the form of a cross-flow reactor, whereby the gas stream can be guided to flow through the cross-flow reactor at least twice.

In accordance with another embodiment of the apparatus of the present invention, the anode is arranged so as to be in contact with the surrounding air.

In accordance with another embodiment of the apparatus of the present invention, the gas stream comprises the exhaust gases in the exhaust pipe of a vehicle.

In accordance with the present invention, a method has also been discovered for the reduction of nitrogen oxides in a gas stream comprising positioning a contact element in the gas stream, the contact element comprising a substrate comprising a solid electrolyte, an anode disposed on the substrate, and a cathode comprising gold disposed on the substrate, whereby the nitrogen oxides are adsorbed and dissociated on the cathode, and applying a voltage across the anode and the cathode to recombine the nitrogen into nitrogen gas, and transport oxygen ions through the substrate from the cathode to the anode. In a preferred embodiment, the method includes measuring the transport of the oxygen ions by means of current measuring means connected to the anode and the cathode, and controlling the application of the voltage depending on the measured value of the current measuring means.

In accordance with one embodiment of the method of the present invention, the anode comprises gold, and applying of the voltage is carried out by means of an AC voltage, and the method includes periodically switching the polarity of the anode and the cathode. In a preferred embodiment, the anode and the cathode consist essentially of gold.

A primary object of the present invention is to provide an improved device for the reduction of nitrogen oxides in the exhaust gases from a combustion engine operating in an environment in which a surplus of oxygen or air is present, and in which the air/fuel mixture of the engine consequently contains more air than would be the case for the stoichiometric mixture (i.e. $\lambda>1$).

The apparatus according to the present invention, which comprises an oxygen ion-conducting substrate having a cathode and an anode which are connected to a voltage source, is based on the principle that gold, as opposed to certain other materials such as platinum, has the property that it generally does not dissociate oxygen. While it is true that gold is inert, it still has a certain catalytic activity, which is considerably higher as regards for example NO or $NO_2$ than as regards oxygen. Consequently, according to the present invention, at least the cathode consists essentially of gold, whereby the oxides of nitrogen surrounding the device are adsorbed and dissociated on the cathode, generating a recombination to nitrogen gas on the cathode while oxygen ions are transported away through the substrate, from the cathode to the anode. Consequently, the present invention generates an oxygen ion current through the substrate, from the cathode to the anode, and a recombination of remaining nitrogen to nitrogen gas on the cathode. By means of the present invention, a high selectivity for $NO_x$ compounds is provided in gases having high levels of oxygen; i.e. the invention also operates at high levels of oxygen in the gas in which $NO_x$ compounds are to be reduced.

In particular, the present invention can be used in connection with a motor vehicle, and, for example, can be used as a complement to an oxidation catalyst intended for purification of HC and CO compounds.

According to one embodiment hereof, the apparatus according to the present invention comprises means for measuring the oxygen ion current being generated in the device. Values constituting measures of the current can then be used for controlling the voltage source, or for example for controlling an EGR valve; i.e., a valve for controlling recirculation of exhaust gases to the engine (EGR=Exhaust gas recirculation).

According to a further embodiment hereof, the present invention comprises means for heating the apparatus hereof to a suitable operating temperature. This provides for stable and regular operation in connection with a reduction in $NO_x$ compounds.

BRIEF DESCRIPTION OF THE DRAWINGS

The present invention will be described in the following detailed description with reference to preferred embodiments and the appended drawings, in which.

DETAILED DESCRIPTION

Figure 1:
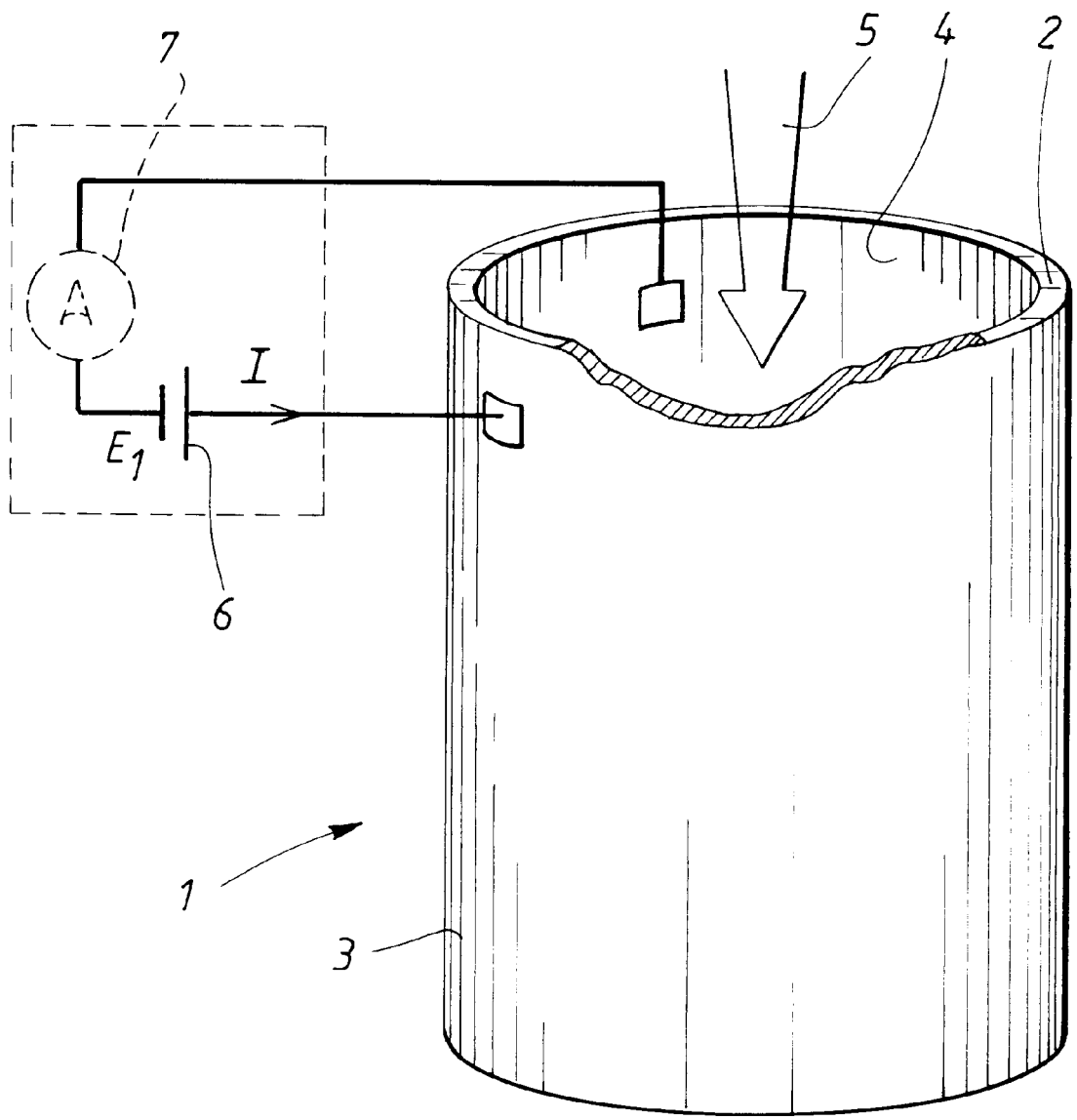
FIG. 1 is a front, perspective, schematic, partially sectional view of a device according to the present invention.

Referring to the Figures, in which like reference numerals refer to like elements thereof, FIG. 1 shows a perspective view of a device according to the present invention which, according to a preferred embodiment, is intended for use in the field of reduction of nitrogen oxides. In particular, the present invention is primarily intended for use in the reduction of nitrogen oxide (NO) and nitrogen dioxide ($NO_2$), by converting these two harmful substances to nitrogen gas ($N_2$). The device comprises a nitrogen oxide reduction element 1 based upon a substrate which is shaped as an essentially tubular component 2 which is manufactured from a solid electrolyte, preferably zirconium dioxide. This material has the property of being a good conductor of oxygen ions. The zirconium dioxide in preferably stabilized; i.e., it is "fixed" in a certain crystal structure which is advantageous as regards its oxygen ion-conducting property. For example, yttrium may be used as a stabilizer.

The outside of the substrate 2 is coated with an outer porous layer 3, which functions as an anode, and the inside of the substrate is coated with an inner porous layer 4, which functions as a cathode. The fact that the layers, 3 and 4, are porous; i.e., that they comprise pores, means that they are pervious to the relevant gases. The inner layer 4 consists essentially of a thin layer of gold, whereas the outer layer 3 is preferably made from gold, but can also be made from some other metal, for example platinum, palladium or rhodium, according to the description which follows. Preferably, the layers, 3 and 4, have a thickness which is approximately 1000 to 2000 Angstrom, but other dimensions are also possible.

The element 1 is particularly suitable for use in a motor vehicle, and in particular in a manner such that a certain amount of exhaust gases from the vehicle's engine (not shown) are guided through the element 1; i.e., in the direction which is indicated by arrow 5. Preferably, a large number of elements 1 can be arranged together, for example next to each other and parallel to each other, in a stack which is arranged in an exhaust flow in a motor vehicle. However, for reasons of clarity, FIG. I shows only one such element 1.

When a gas containing $NO_x$ compounds is guided through the element 1, these compounds will be adsorbed on the inner layer 4, which forms the cathode. In this manner, a selective dissociation; i.e., a decomposition, of $NO_x$ compounds takes place so that negative oxygen ions, $0^{2-}$, are generated at the cathode 4. Furthermore, the anode 3 and the cathode 4 are electrically connected to a first voltage source 6. In this manner, the oxygen ions are transported away through the oxygen ion-conducting plate 2 by means of the voltage $E_1$ which is applied by means of the voltage source 6, whereas remaining nitrogen atoms recombine into molecular nitrogen, $N_2$, and return into the gas phase. At the anode 3, the oxygen ions also recombine into molecular oxygen, $0_2$, and return into the gas phase.

The voltage $E_1$ consequently applied so as to transport the oxygen ions from the cathode 4, through the substrate 2, to the anode 3. In this manner, $NO_x$ compounds in a gas being guided through the element I can be reduced into nitrogen gas.

According to the present invention, the electrodes, 3 and 4, can be formed in various manners, for example as thin, generally coating, porous layers, which are preferably arranged on both sides of the substrate 2. However, other ways of forming the electrodes, 3 and 4, are also possible. In order to accomplish an optimized transport of oxygen ions, the electrodes, 3 and 4, extend over a substantial area along the surface of the substrate 2.

In the electric circuit consisting of the plate 2, the anode 3 and the cathode 4, as well as the first voltage source 6, an ammeter 7 is arranged for measuring the oxygen ion current I generated in the circuit. The measured current I constitutes a measure of the concentration of $NO_x$ compounds in the sensor's 1 environment. The measuring of the current I is described in Swedish Patent Application No. 9303664-8, filed on Nov. 8, 1993, by the assignee of the present application.

The element 1 provides a reduction of $NO_x$ compounds which is highly selective; i.e., the oxygen ions generating the current I originate mainly from $NO_x$ compounds (and not from any molecular oxygen) occurring in the gas which surrounds the element 1. For example, diesel exhaust gases contain 5 to 18% oxygen, which can be adsorbed, dissociated and ionized on the surface, thereby consuming a significant amount of capacity during transport of the oxygen ions. However, due to the high selectivity of gold for $NO_x$ compounds, the contribution of the molecular oxygen ($0_2$) to the ion current I is of a relatively insignificant magnitude. The selectivity of the invention depends on the arrangement of the electrodes, 3 and 4, of which at least the cathode 4 consists of gold. According to a possible embodiment hereof, both electrodes, 3 and 4, consist of gold. As is explained above, the reason for this increased selectivity is that gold generally does not dissociate oxygen (as opposed to platinum, for example) and involves a catalytic activity which is considerably higher as regards $NO_x$ compounds than oxygen. In this manner, element 1 is adapted for dissociation of $NO_x$ compounds which is considerably higher than the dissociation of oxygen. In this manner, the harmful $NO_x$ compounds in the exhaust gases are converted into nitrogen gas, whereas any oxygen in the exhaust gases contributes only to a very low degree to the above-mentioned oxygen ion current and consequently does not consume any capacity, thereby assuring a high degree of efficiency of the $NO_x$ reduction. In turn, this means that the present invention is particularly suitable for reduction of $NO_x$ compounds in gases having a high or varying oxygen content.

According to a further embodiment of the present invention, the cathode 4, and alternatively both the cathode 4 and the anode 3, consists essentially of gold together with a small amount of a stabilizing material, for example platinum. This stabilizes the gold without destroying its properties. The amount of platinum is chosen so that it constitutes a relatively low amount in relation to the amount of gold of the respective electrode. In this manner, the selective property of the gold is not significantly affected.

Furthermore, a thin stabilizing layer of, for example, magnesium oxide or a metal (for example platinum) can be arranged between the anode 3 and the substrate 2 or between the cathode 4 and substrate 2, respectively, so as to improve the adhesive effect of the gold to the substrate 2. The thickness of the stabilizing layer is chosen depending on the choice of material, but it is preferably relatively thin and porous, which means that it will not prevent the oxygen ions from being transported between the substrate and the respective electrode.

Figure 2:
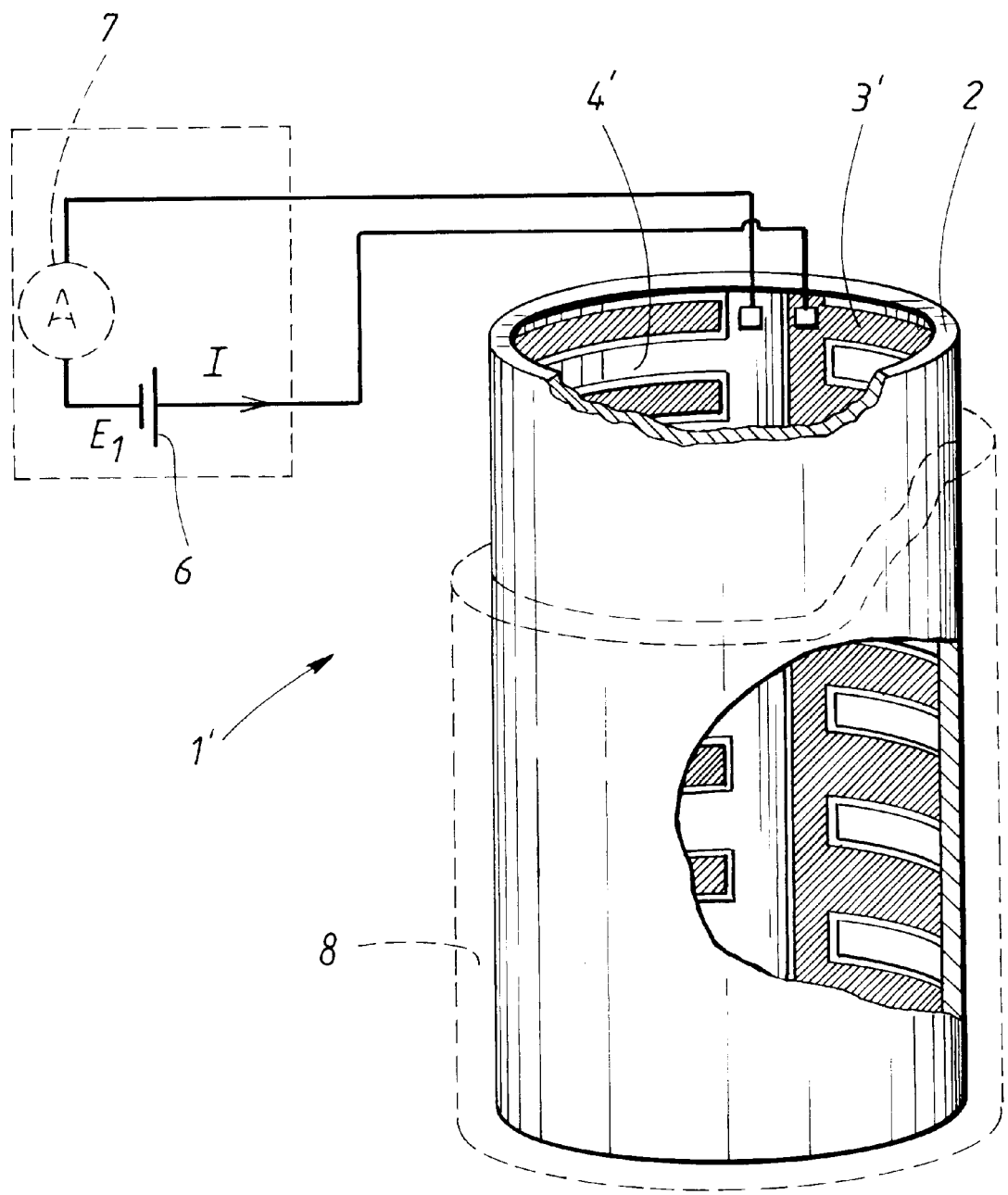
FIG. 2 is a front, perspective, schematic, partially sectional and cut-away view showing the device according to the present invention according to an alternative embodiment.

FIG. 2 shows a perspective view of an element 1' according to an alternative embodiment hereof, which comprises an anode 3' and a cathode 4', both of which are arranged on the inside of an essentially tubular substrate 2. The anode 3'and the cathode 4' are electrically connected to the voltage source 6', and can also be connected to an ammeter 7. Preferably, the anode 3' and the cathode 4' are arranged in a linear form with a plurality of transverse lines which are arranged so that they project essentially perpendicularly from the first line, and so that they protrude into each other. Furthermore, the conductive paths, 3' and 4', are preferably arranged as close and as dense as possible. By means of this arrangement, the active boundary surface between each electrode, 3' and 4', and the substrate 2 where the recombination into nitrogen gas and the transport of negative oxygen ions occurs, is as large as possible. This contributes to a high oxygen ion current I, and consequently, to a high degree of reduction of $NO_x$ compounds.

According to an alternative embodiment of the present invention which is shown in FIG. 2, the element 1' is surrounded by a tubular element 8 which constitutes a carrying support tube which carries the substrate 2 with its electrodes, 3' and 4'. The tubular element 8, the inner dimensions of which essentially correspond to the outer dimensions of the element 1', can be provided with a heating device 8, which, in turn, is provided with means (not shown) for heating of the element 1', for example in the form of a resistive conductor such as a heating wire, which is connected to a further voltage source (not shown). The voltage of this voltage source is chosen so that the heating wire can heat the substrate 2 to a suitable operating temperature, at which the substrate 2 conducts oxygen ions. This makes it possible for the above-mentioned current I of oxygen ions to flow between the cathode 4' and the anode 3'. The normal operating temperature of the element 1 is approximately 300 to 800° C..

According to a further alternative hereof, such a heating wire can also be enclosed within the substrate 2 (not shown in the drawing). Furthermore, it should be noted that the heating device 8 can also be used in connection with the embodiment shown in FIG. 1. Furthermore, during use of the present invention in connection with combustion processes with exhaust gases at a very high temperature, the exhaust gases themselves may be used for heating the substrate 2 to the temperature at which it presents a high conductivity for oxygen ions. Consequently, in such a case no particular additional heating device is required.

The devices according to FIGS. 1 or 2 are suitable for use in motor vehicles, for reduction of $NO_x$ compounds in exhaust gases from the engine. The exhaust gases from the vehicle's engine are guided through an exhaust pipe (not shown) and the element 1 (alternatively 1'). The exhaust pipe can also be connected to an exhaust gas catalyst (not shown) of a conventional type, which in such case is arranged either upstream or downstream of the element 1 (alternatively 1'). The exhaust pipe can also constitute a branch pipe provided for a partial flow of exhaust gases from the engine. Preferably, a large number of $NO_x$ reduction elements 1 (1') are arranged parallel to each other, so that a high reduction effect can be obtained.

FIGS. 1 and 2 only show the principle for reduction of $NO_x$ compounds in exhaust gases. It should be obvious that, for example, the size of the anode 3 or the cathode 4 or the diameter of the tube 9 can be varied so as to provide an optimal degree of purification for the particular use of the present invention. Furthermore, several flows can be arranged in parallel or in series so as to improve the degree of purification.

According to a possible embodiment hereof, both the anode 3 and the cathode 4 can consist essentially of gold, and the applied voltage $E_1$ can be in the form of an AC voltage. In this manner, the polarity of the anode 3 and the cathode 4, respectively, can be switched periodically.

Figure 3:
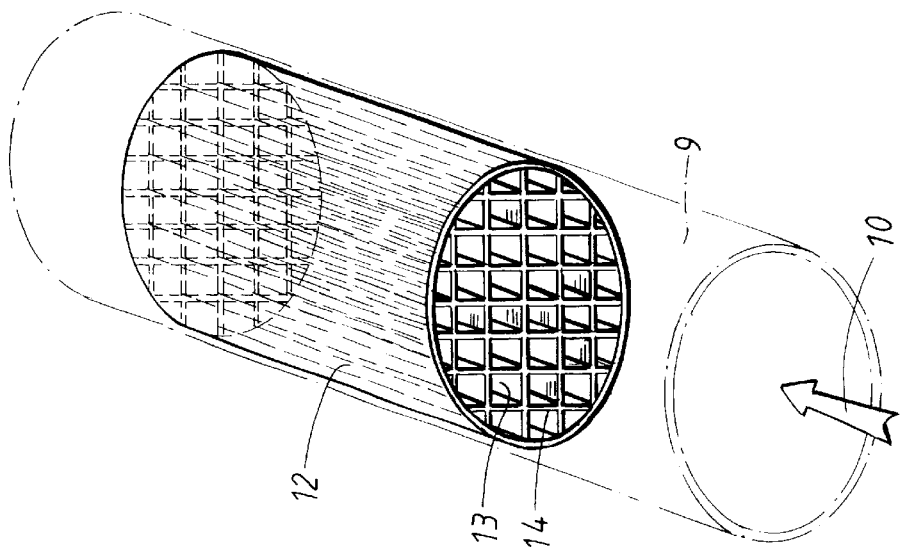
FIG. 3 is a side, perspective, schematic view of a nitrogen oxide reduction unit of the present invention which can be used in connection with a combustion engine.

FIG. 3 shows a nitrogen oxide reduction unit 12 according to a further embodiment of the present invention, which can be used to convert $NO_x$ compounds in the exhaust gases from a combustion engine. To this end, the reduction unit 12 is arranged in an exhaust pipe 9 in connection with a combustion engine (not shown) in a motor vehicle. The exhaust pipe 9 can also be in the form of a conduit for a partial flow of exhaust gases. The exhaust gases from the engine are guided through the exhaust pipe 9 in the direction indicated by arrow 10. The reduction unit 12 is based around a plurality of ducts 13 through which the exhaust gases are guided. The ducts 13 extend in a direction which is essentially parallel to the direction in which the exhaust pipe 9 extends. Furthermore, each duct 13 is defined by walls 14 which comprise an oxygen ion-conducting, ceramic material of the same type as the substrate 2, according to the above discussion. As regarded along a cross-section, the walls 14 form an essentially checked pattern having square or rectangular sides. According to this embodiment, the reduction unit is dimensioned with a distance of approximately 1 to 4 mm between two walls which face each other in a particular duct 13. This corresponds to a use in connection with a motor vehicle.

Generally, each duct 13 in the reduction unit 12 corresponds to the element 1 or 1', respectively, as shown in FIGS. 1 and 2, respectively. It should be noted that the ducts 13 can be formed with different cross-sections, for example square, rectangular, circular or triangular cross-sections.

Figure 4:
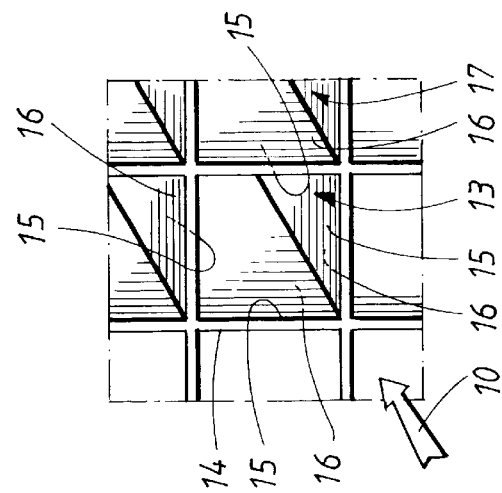
FIG. 4 is a side, enlarged, detailed view of the nitrogen oxide reduction unit according to FIG. 3.

FIG. 4 shows, in a slightly enlarged view, a small portion of the reduction unit 12 comprising a particular duct 13 and a plurality of further, adjacent ducts 17 which are positioned immediately adjacent to the first-mentioned duct 13. The duct 13 is defined by four walls, the insides of which operate as a cathode 15. To this end, the cathode 15 consists of a coating on the inside of the duct 13, the wall 14 being completely of partially coated with gold. In a corresponding manner, an anode 16 is defined by the inner walls which define the respective adjacent duct 17. To this end, the anode 16 consists of a coating on the walls 14 which delimit the respective duct 17, which coating is constituted by a metal, preferably gold, platinum or another suitable metal.

With renewed reference to FIG. 3, it is shown that the reduction unit 12 is formed by a carrier substrate 14 having a plurality of anodes 16 and cathodes 15 which are formed by coatings in adjacent ducts. A particular duct, the inner walls of which define an anode, will be surrounded by four adjacent ducts (two in the transverse direction and two in the vertical direction), the inner walls of which form a cathode, and vice versa.

In a manner which corresponds to what has been stated above, each cathode 15 and anode is provided with connectors to a voltage source (not shown in FIG. 4). In this manner, oxygen ions can be transported through the walls 14, from the cathode 15 to the anode 16, when exhaust gases containing $NO_x$ compounds are guided through the respective duct 13. In turn, the simultaneous recombination of remaining nitrogen into $N_2$ on the cathode leads to a reduction of harmful $NO_x$ compounds in the exhaust gases.

According to an alternative of the embodiment shown in FIGS. 3 and 4, the respective adjacent ducts 17 (i.e., the ducts 17, the inner walls 16 of which form anodes) can be blocked, thereby allowing no exhaust gases to be guided therethrough. Since the oxygen ion current is generated in each duct 13 (i.e., the duct 13, the inner walls 15 of which form cathodes) and is guided in a direction from the cathode 15 to the anode 16, a higher degree of efficiency of the reduction unit 12 is provided if no exhaust gases are allowed to be guided through the ducts, the inner walls 16 of which form anodes.

According to a further alternative hereof, two reduction units 12 can be arranged after one another, the ducts 13 (the inner walls 15 of which form cathodes) of the upstream reduction unit being arranged in line with the ducts 17 (the inner walls 16 of which form anodes) of the downstream reduction unit, or vice versa. In this manner, essentially the entire amount of exhaust gas which is guided through the exhaust pipe 9 will pass through ducts 13 which form cathodes. In turn, this will provide improved efficiency for the $NO_x$ reduction.

Figure 5:
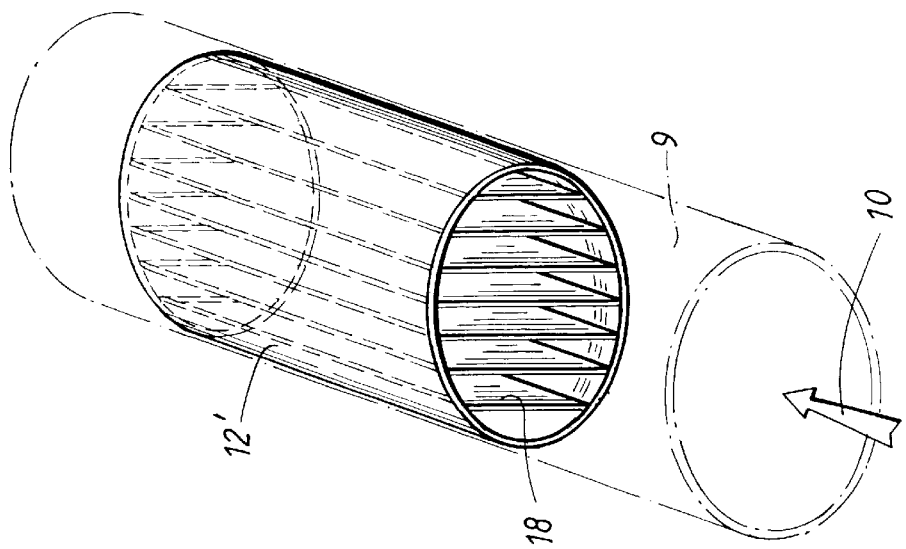
FIG. 5 is a side, perspective, schematic view of an alternatively designed nitrogen oxide reduction unit according to the present invention.

FIG. 5 shows a reduction unit 12' according to a further embodiment which, in this case, is formed by a number of plates 18 which are arranged essentially parallel to the longitudinal extension of the exhaust pipe 9. In this manner, ducts or gaps 19 are formed, through which exhaust gases containing $NO_x$ compounds can be guided. Also in this case, the exhaust gases flow in the direction indicated by arrow 10. The plates 18 form a plurality of substrates which are formed by a oxygen ion-conducting material, which corresponds to the substrate 2 according to the above explanation. On each side of each plate 18, a coating is formed which defines an anode on one side of each plate 18 and a cathode on the other side of each plate 18. The anodes and cathodes can be arranged in two different ways. Either they are arranged so that an anode of a particular plate faces a cathode of an adjacent plate, or so that an anode of a particular plate faces an anode of an adjacent plate. In the same manner as stated above, the anodes and cathodes are connected to a voltage source (not shown) for transporting oxygen ions from the cathodes through each plate 18.

A particularly high degree of efficiency can be obtained if the plates 18 are arranged so that the cathodes on two adjacent plates face each other and the anodes on two adjacent plates face each other, and if no exhaust gases are allowed to flow through the interspaces which are defined by the anodes. This is obtained by blocking the ducts which are defined by anodes which face each other.

According to an alternative embodiment hereof, two reduction units 12' can be arranged after one another. In this regard, the interspaces, the inner walls of which constitute cathodes, of the upstream reduction unit are arranged in line with the interspaces, the inner walls of which constitute anodes, of the downstream reduction unit, or vice versa. In this manner, essentially all the amount of exhaust gases flowing through the exhaust pipe 9 will pass interspaces which constitute cathodes.

Figure 6:
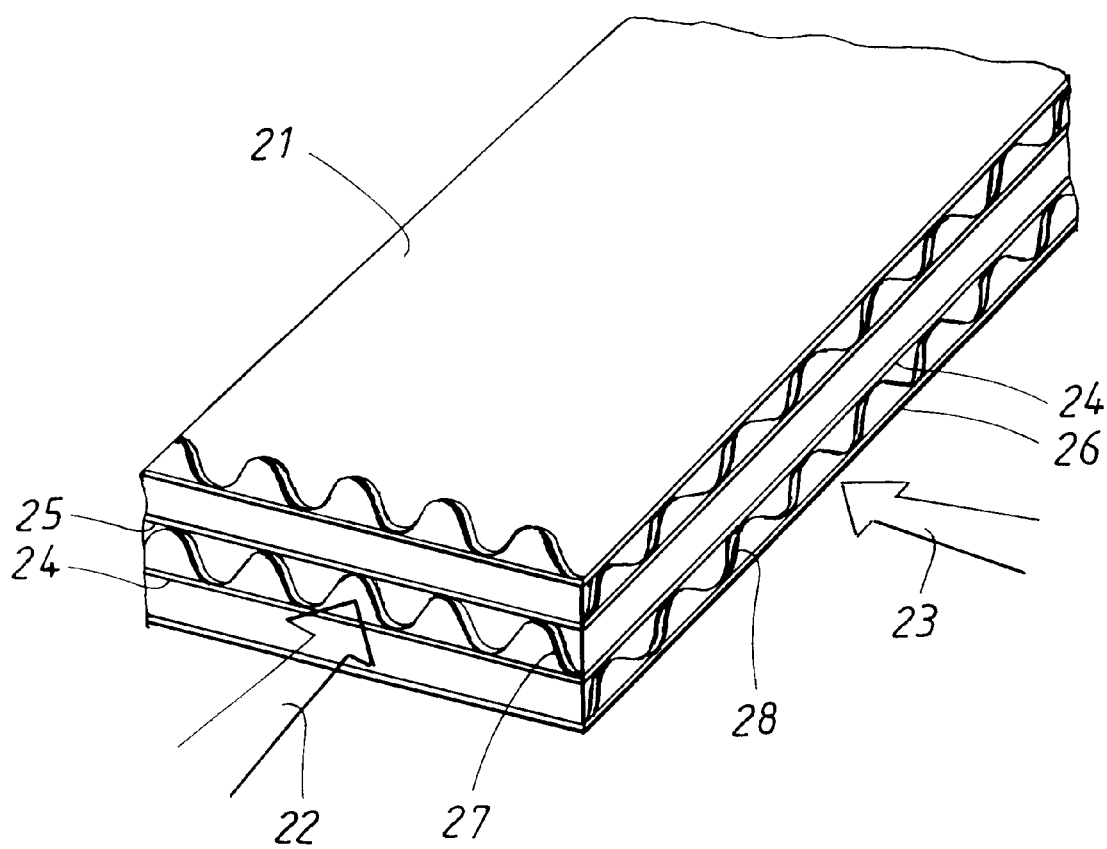
FIG. 6 is a side, perspective, partial view of a nitrogen oxide reduction unit according to a further embodiment of the present invention.

FIG. 6 discloses a reduction unit 21 according to a further embodiment hereof, which is adapted to guide the exhaust gases from an engine through a cross-flow reactor. The purpose of this arrangement is to provide quick heating of exhaust gases by guiding them twice through the reduction unit 21. According to this embodiment, a flow a exhaust gases is guided in a direction which is indicated by arrow 22 and through the reduction unit 21. After that, the flow of exhaust gases is guided through a further conduit (not shown) and back towards the reduction unit 21 along a further direction which is indicated by arrow 23. The flow in the direction 22 is guided past two plate-like elements, 24 and 25, (constituting a cathode) whereas the flow in the direction 23 is guided past the opposite side of the element 24 and a further plate-like element 26 (constituting an anode). Each element 24, 25 and 26 has a design and operation which correspond to the plates 18 in FIG. 5. The elements 24, 25, and 26 are fixed in the structure shown in FIG. 6 by means of two further elements, 27 and 28, respectively, which are preferably wave-shaped and are adapted to provide stiffness to the complete assembly. Also the wave-shaped elements, 27 and 28, can be coated with thin anode and cathode layers, according to the principles described above. Furthermore, the elements 27 and 28 can be arranged with such orientation that any of the flows 22 or 23 is blocked.

In the case where the reduction unit 21 does not have to be heated in the manner described above, the ducts formed by the elements 24 and 25, and which consequently form an anode, can alternatively be blocked so that no exhaust gases are guided through these ducts. Instead, they can be in contact with the surrounding air, which means that the flow which is indicated by the arrow 23 instead is constituted by air.

During practical measurements which have been made with the device according to the present invention, at an operating temperature of 500° C. and an operating voltage $E_1$ (cf. FIG. 1) of 1.0 V, a reduction of more than 90% of the NO and $NO_2$ content in a sample gas has been obtained. During these measurements, the oxygen concentration was 10% and the NO content was 1000 ppm. This indicates that the present invention provides a considerably higher degree of reduction of $NO_x$ compounds than previously known systems.

The present invention is not limited to the above-mentioned embodiments shown in the drawings, but can be varied within the scope of the appended claims. For example, it should be realized that the elements 1 and 11, respectively, can be manufactured in the form of a circular or square tube, or in the form of another geometrical shape. Also, the anode 3 and the cathode 4 can be designed in different ways, for example as two helical conductive patterns. Furthermore, the two electrodes 3, 4 can be positioned on the same side of the substrate 2 or on each side of the substrate 2.

In the case where the cathode 4 and the anode 3 are connected to the ammeter 7 (cf. FIGS. 1 and 2), the ammeter 7 and the first voltage source 6 can constitute components in a control unit, the purpose of which is to control the first voltage source 6 depending on the current I being measured in the circuit, which current depends on the activity on the cathode 4. In this regard, the control unit can be adapted to control the voltage in the first voltage source 6 to a value which is adapted to the amount of NOX compounds which should be reduced. In this manner, the current consumption of the first voltage source 6 can be minimized.

In the embodiments shown in FIGS. 3–5, the exhaust pipe 9 can be connected to an oxidation catalyst (not shown) for purification of HC and CO compounds. In this case, the oxidation catalyst can be positioned either upstream or downstream of the reduction unit 12 or 12', respectively.

Furthermore, it is possible to arrange the electrodes, 15 and 16, according to FIGS. 4 and 5, on the same side of the substrate 14, i.e. they need not be placed on each side of the substrate 14. Furthermore, a particular duct 13 (cf. FIG. 3) can be provided with inner walls with separate fields which constitute anode and cathode, respectively. In this manner, a reduction unit 12 can be manufactured so that all the ducts 13 are formed by identical components.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Apparatus for the reduction of nitrogen oxides in a gas stream comprising:

an oxygen ion conducting substrate, at least one anode disposed on said substrate, at least one cathode disposed on said substrate, a voltage source connected to said anode and said cathode, and a plurality of plates including a first side and a second side defining a plurality of longitudinally extending ducts for guiding said gas stream, at least one of said first and second sides of said plurality of plates comprising said cathode and the other side of said first and second sides of said plurality of plates comprising said anode, said plurality of plates including at least one pair of adjacent plates, and including at least one of said first and second sides of said at least one pair of said adjacent plates comprising a pair of cathodes facing each other, said anode and said cathode comprising conductive patterns, said cathode comprising gold, whereby said nitrogen oxides are adsorbed and dissociated on said cathode, nitrogen may recombine into nitrogen gas on said cathode, and oxygen ions are transported through said substrate from said cathode to said anode.

2. The apparatus of claim 1 wherein said plurality of longitudinally extending ducts includes said other of said first and second sides of said at least one pair of said adjacent plates comprising said anodes are shaped so as to block the passage of said gas stream therethrough.

3. The apparatus of claim 1 wherein said substrate comprises a first duct comprising said anode and a second duct comprising said cathode, said first and second ducts disposed in the form of a cross-flow reactor, whereby said gas stream can be guided to flow through said cross-flow reactor at least twice.

4. The apparatus of claim 1 wherein said anode is arranged so as to be in contact with the surrounding air.

5. The apparatus of claim 1 wherein said gas stream comprises the exhaust gases in the exhaust pipe of a vehicle.

6. The apparatus of claim 1 wherein said cathode consists essentially of gold.

7. The apparatus of claim 1 wherein said anode comprises a material selected from the group consisting of gold, palladium and rhodium.

8. The apparatus of claim 7 wherein said anode consists essentially of said material.

9. The apparatus of claim 1 wherein said cathode includes a stabilizing material.

10. The apparatus of claim 9 wherein said anode includes a stabilizing material.

11. The apparatus of claim 10 wherein said stabilizing material comprises platinum.

12. The apparatus of claim 1 wherein said oxygen ion conducting substrate comprises stabilized zirconium dioxide.

13. The apparatus of claim 1 including current measuring means for measuring the transport of said oxygen ions through said substrate and control means for controlling said voltage source based on said measured value of said current measuring means.

14. The apparatus of claim 1 including heating means for heating said substrate.

15. The apparatus of claim 14 wherein said voltage source comprises a first voltage source, said heating means comprises a resistance conductor, and including a second voltage source for said resistance conductor.

16. The apparatus of claim 1 wherein said anode and said cathode comprise a porous material.

17. The apparatus of claim 1 wherein said anode and said cathode comprise a conducting pattern including a substantially linear portion and a plurality of transverse portions extending substantially perpendicularly from said substantially linear portion.

18. The apparatus of claim 1 wherein said substrate comprises a plurality of walls providing a plurality of adjacent ducts for guiding said gas stream, said anode and said cathode comprising coatings on at least one of said plurality of walls forming said plurality of adjacent ducts.

19. The apparatus of claim 18 wherein said plurality of adjacent ducts comprises a first duct and a second duct adjacent to said first duct, and said walls comprise at least one inner wall of said first and second ducts, said cathode comprising a coating on said at least one inner wall of said first duct and said anode comprises a coating on said at least one inner wall of said second duct.

* * * * *